United States Patent
Suzuki et al.

(10) Patent No.: US 8,052,863 B2
(45) Date of Patent: Nov. 8, 2011

(54) GAS SENSOR CONTROL APPARATUS DESIGNED TO ENSURE ACCURACY OF MEASUREMENT IN GAS SENSOR

(75) Inventors: Toshiyuki Suzuki, Handa (JP); Tomoo Kawase, Aichi-ken (JP); Eiichi Kurokawa, Okazaki (JP); Yohei Kawaki, Toyota (JP)

(73) Assignee: Denso Corporation, Kariya (JP)

( * ) Notice: Subject to any disclaimer, the term of this patent is extended or adjusted under 35 U.S.C. 154(b) by 932 days.

(21) Appl. No.: 12/034,078

(22) Filed: Feb. 20, 2008

(65) Prior Publication Data
US 2008/0197022 A1 Aug. 21, 2008

(30) Foreign Application Priority Data
Feb. 20, 2007 (JP) ................................. 2007-039907

(51) Int. Cl.
*G01N 27/417* (2006.01)
(52) U.S. Cl. .......................... 205/784; 204/425; 204/406
(58) Field of Classification Search .................. 204/406, 204/425, 426; 205/784; 73/23.31, 23.32
See application file for complete search history.

(56) References Cited

U.S. PATENT DOCUMENTS

| 4,419,190 A | 12/1983 | Dietz et al. |
| 2004/0195097 A1 | 10/2004 | Suzuki et al. |
| 2004/0217001 A1* | 11/2004 | Hada et al. ..................... 204/424 |
| 2004/0222094 A1* | 11/2004 | Ieda et al. ..................... 204/424 |

FOREIGN PATENT DOCUMENTS

| JP | 57-187646 | 11/1982 |
| JP | 2000-227364 | 8/2000 |
| JP | 2000-329739 | 11/2000 |
| JP | 2004-251891 | 9/2004 |

OTHER PUBLICATIONS

Japanese Office Action dated Dec. 9, 2008 issued in corresponding Japanese Application No. 2007-039907, with English translation.

* cited by examiner

*Primary Examiner* — Kaj K Olsen
(74) *Attorney, Agent, or Firm* — Nixon & Vanderhye P.C.

(57) ABSTRACT

The gas sensor control apparatus develops a first voltage based on a first reference voltage at a negative terminal of a gas sensor device through a resistor and a second voltage based on a second reference voltage at a positive terminal of the gas sensor device. A controller samples through the resistor a sensor current, as created upon the development of the first and second voltage for measuring the concentration of gas. When the impedance of the gas sensor device is measured, the controller alternates the first voltage across the first reference voltage. The value (i.e., a zero-point) of the voltage applied to the gas sensor device when the sensor current is zero (i.e., 0 mA) depends upon the first and second reference voltages. The zero-point is corrected by regulating the second reference voltage to match an applying voltage characteristic to the gas sensor device correctly.

5 Claims, 5 Drawing Sheets

GAS SENSOR CONTROL APPARATUS DESIGNED TO ENSURE ACCURACY OF MEASUREMENT IN GAS SENSOR

CROSS REFERENCE TO RELATED DOCUMENT

The present application claims the benefits of Japanese Patent Application No. 2007-39907 filed on Feb. 20, 2007, the disclosures of which are totally incorporated herein by reference.

BACKGROUND OF THE INVENTION

1. Technical Field of the Invention

The present invention relates generally to a gas sensor control apparatus which controls an operation of a gas sensor which is equipped with a solid electrolyte layer and works to measure the concentration of gas, and more particularly to such a control apparatus designed to ensure the accuracy of measurement in a gas sensor.

2. Background Art

Limiting current oxygen sensors are used as air-fuel (A/F) ratio sensors designed to measure the concentration of oxygen ($O_2$) contained in exhaust emissions of motor vehicle engines to determine an air-fuel ratio of a mixture charged into the engine. A typical one of such oxygen sensors is equipped with a sensor device made up of a solid electrolyte layer made of, for example, zirconia and a pair of electrodes affixed to the solid electrolyte layer. The measurement of concentration of oxygen is achieved by applying the voltage to the solid electrolyte layer through the electrodes to produce a flow of electrical current through the sensor device as a function of the concentration of oxygen and sampling the electrical current for determining the air-fuel ratio of the mixture.

Ensuring the accuracy of measuring the concentration of oxygen requires control of the voltage to be applied to the sensor device. A variety of techniques are proposed to control the voltage to be applied to the sensor device. For example, Japanese Patent First Publication No. 2004-251891 teaches a gas concentration measuring apparatus which is designed to control the voltage to be applied to the sensor device using an applying voltage characteristic, as defined in the form of a first-order line (will also be referred to as an applying voltage characteristic line below) and to measure the concentration of oxygen in a wide range using an electric current (will also be referred to as a sensor current below) flowing through the sensor device. The gas concentration measuring apparatus also works to change the applying voltage characteristic based on the width of a limiting current range (i.e., a flat range of an output of the sensor device) appearing per given level of the concentration of oxygen within a gas concentration measuring range.

Specifically, the gas concentration measuring apparatus works to change the inclination of the applying voltage characteristic line to bring the voltage to be applied to the sensor device into within the limiting current range (i.e., the flat range) at each of the levels of the concentration of oxygen. The width of the flat ranges of the applying voltage characteristic may, however, be different between sensors. This may not be eliminated only by correcting the inclination of the applying voltage characteristic line. The control of the voltage to be applied to the sensor device has sill left room for improvement.

SUMMARY OF THE INVENTION

It is therefore a principal object of the invention to avoid the disadvantages of the prior art.

It is another object of the invention to provide a gas sensor control apparatus designed to permit control of voltage to be applied to a gas sensor device to be corrected to ensure the accuracy of measurement in the gas sensor device.

According to one aspect of the invention, there is provided a gas sensor control apparatus which may be employed with an A/F ratio sensor to determine an air-fuel ratio of a mixture supplied to an automotive engine for use in combustion control of the engine. The gas sensor control apparatus is designed to control an operation of a gas sensor device equipped with a solid electrolyte body and a first and a second electrode affixed to opposed surfaces of the solid electrolyte body and comprises: (a) a sensor current sampling resistor connected in series to a first terminal that is one of a positive and a negative terminals which leads to the first electrode of the gas sensor device; (b) a first voltage supply circuit works to develop a first voltage based on a first reference voltage at the first terminal leading to the gas sensor device through the sensor current sampling resistor; (c) a second voltage supply circuit working to develop a second voltage based on a second reference voltage at a second terminal that is other of the positive and negative terminals which leads to the second electrode of the gas sensor device; and (d) a controller working to sample through the sensor current sampling resistor a sensor current that is an electric current flowing through the gas sensor device upon application of voltage across the gas sensor device through the first and second terminals resulting from development of the first and second voltage at the first and second terminals and to produce a signal based on the sensor current which is a function of concentration of a given gas. When it is required to measure an impedance of the gas sensor device, the controller alternates the first voltage across the first reference voltage and samples and outputs a resulting change in the sensor current as representing the impedance of the gas sensor device.

Specifically, in operation of the gas sensor control apparatus, the first voltage, as created based on the first reference voltage, is applied to the first terminal of the gas sensor device, while the second voltage, as created based on the second reference voltage, is applied to the second terminal of the gas sensor device. The voltage that is developed by a difference between the first and second voltages is applied across the gas sensor device. The controller monitors the voltage appearing at either of terminals of the sensor current sampling resistor to sample the sensor current flowing through the gas sensor device arising from the application of the voltage thereto. The controller also alters the output of the first voltage supply circuit across the first reference voltage to apply an ac voltage to the gas sensor device to measure the impedance of the gas sensor device. The impedance may be used for controlling activation of the gas sensor device. For example, the impedance is employed to control the temperature of the gas sensor device through a heater.

The value (i.e., a zero-point) of the voltage applied to the gas sensor device when the sensor current is zero (i.e., 0 mA) depends upon the first and second reference voltages. The zero-point may, therefore, be altered or corrected by regulating either of the first and second reference voltages. Such correction enables the voltage to be applied to the gas sensor device to be determined correctly within a desired range of an output characteristic of the gas sensor device. The correction of the zero-point is made, for example, in bench-tests before shipment of the gas sensor control apparatus.

The correction of the zero-point is achieved by altering or regulating the second reference voltage. The first reference voltage is a reference voltage both for sampling the sensor current and for developing the amplitude of the ac voltage to measure the impedance of the gas sensor device. Therefore, altering the first reference voltage to correct the zero-point may result in adverse effects on other operations of the gas sensor control apparatus. For example, the altering of the reference voltage results in an offset error in sampling the sensor current. In contrast, the second reference voltage does not contribute directly to the sampling of the sensor current or the measurement of the impedance. Specifically, the second voltage supply circuit is provided independently of the sensor current sampling resistor and a component of the first voltage supply circuit to develop the ac voltage. The regulation of the second reference voltage, therefore, results in no effects on the operations of the gas sensor control apparatus.

In the preferred mode of the invention, an IC such as an ASIC (Application Specific Integrated Circuit) is provided on which the first voltage supply circuit is fabricated. The second voltage supply circuit has a reference voltage circuit which works to create the second reference voltage and is located outside the IC, thus facilitating ease of correcting the second reference voltage.

The second voltage supply circuit includes a voltage divider which has a resistor to produce a fraction of an output of a constant voltage source to create the second reference voltage. The correction of the second reference voltage may be achieved by altering resistance values of the resistors.

The second voltage supply circuit includes a bridge circuit made up of four resistors and a first and a second switches disposed at a high potential side and a low potential side of the bridge circuit, respectively. The controller turns on and off the first and second switches alternatively to alternate the first voltage across the first reference voltage. Altering the first reference voltage requires changing resistance values of all the resistors of the bridge circuit. The regulation of the second reference voltage to correct the zero-point is, therefore, useful in this structure.

In the case where the first voltage supply circuit is, as described above, fabricated on the IC, the altering of the first reference voltage requires the resistors of the bridge circuit to be installed outside the IC and additional terminals to be provided on the IC. This need is, however, eliminated by regulating the second reference voltage to correct the zero-point.

The second voltage supply circuit may be designed to amplify the sensor current, as sampled through the sensor current sampling resistor, to control the second voltage, as developed at the second terminal. For instance, the second voltage supply circuit is made to include an inverting or non-inverting amplifier in which the second reference voltage is inputted into one of input terminals of the amplifier, and the sensor current is inputted to the other terminal. The amplification factor of the amplifier may be regulated by changing a ratio of an input resistance and a feedback resistance. The inclination of an applying voltage characteristic used to determine the voltage to be applied to the gas sensor device may be corrected by regulating the amplification factor.

According to the second aspect of the invention, there is provided a method of controlling a voltage to be applied to a gas sensor device equipped with a solid electrolyte body and a first and a second electrode affixed to opposed surfaces of the solid electrolyte body through a gas sensor control apparatus. The gas sensor control apparatus includes (a) a sensor current sampling resistor connected in series to a first terminal that is one of a positive and a negative terminals which leads to the first electrode of the gas sensor device, (b) a first voltage supply circuit works to develop a first voltage based on a first reference voltage at the first terminal leading to the gas sensor device through the sensor current sampling resistor, (c) a second voltage supply circuit working to develop a second voltage based on a second reference voltage at a second terminal that is other of the positive and negative terminals which leads to the second electrode of the gas sensor device, and (d) a controller working to control the second voltage to determine and apply a voltage across the gas sensor device through the first and second terminals based on a given applying voltage characteristic and to sample through the sensor current sampling resistor a sensor current that is an electric current flowing through the gas sensor device resulting from application of the voltage across the gas sensor device to produce a signal based on the sensor current which is a function of concentration of a given gas. When it is required to measure an impedance of the gas sensor device, the controller alternates the first voltage across the first reference voltage and samples and outputs a resulting change in the sensor current as representing the impedance of the gas sensor device. The method comprises sampling an output characteristic of the gas sensor device, and correcting the applying voltage characteristic based on the sampled output characteristic so as to bring the voltage applied to the gas sensor device into agreement with a desired one.

BRIEF DESCRIPTION OF THE DRAWINGS

The present invention will be understood more fully from the detailed description given hereinbelow and from the accompanying drawings of the preferred embodiment of the invention, which, however, should not be taken to limit the invention to the specific embodiments but are for the purpose of explanation and understanding only.

In the drawings.

DESCRIPTION OF THE PREFERRED EMBODIMENTS

Figure 1:
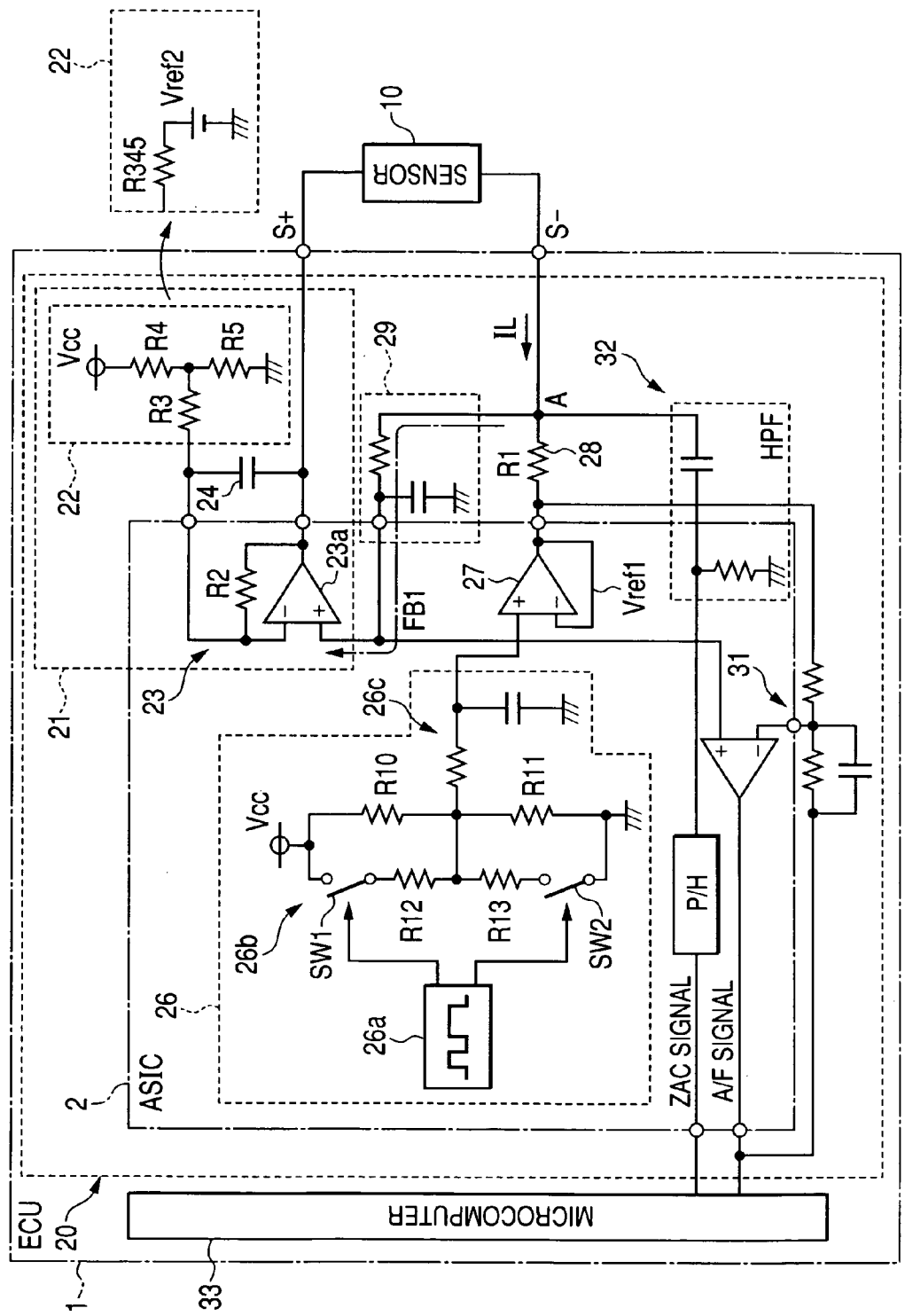
FIG. 1 is a circuit diagram which shows an electric structure of a gas sensor control apparatus according to the invention.

Referring to the drawings, wherein like reference numbers refer to like parts in several views, particularly to FIG. 1, there is shown a gas sensor control apparatus according to the invention which is designed as an air-fuel ratio measuring apparatus to measure the concentration of oxygen ($O_2$) contained in exhaust emissions from an internal combustion engine mounted in an automotive vehicle as a function of an air-fuel (A/F) ratio of a mixture charged into the engine. The output from the air-fuel ratio measuring apparatus is used as representing the air-fuel ratio in an air-fuel ratio control system implemented by an electronic control unit (ECU). The air-fuel ratio control system works to perform a stoichiometric burning control to regulate the air-fuel ratio of the mixture around the stoichiometric air-fuel ratio in the feedback mode or a lean-burn control to bring the air-fuel ratio to within a given lean range in the feedback mode.

The air-fuel ratio measuring apparatus generally includes an engine ECU 1 and an air-fuel (A/F) ratio sensor which is equipped with a planer sensor device 10 (also called a laminated sensor device). The sensor device 10 has a sectional structure, as illustrated in FIG. 2.

Figure 2:
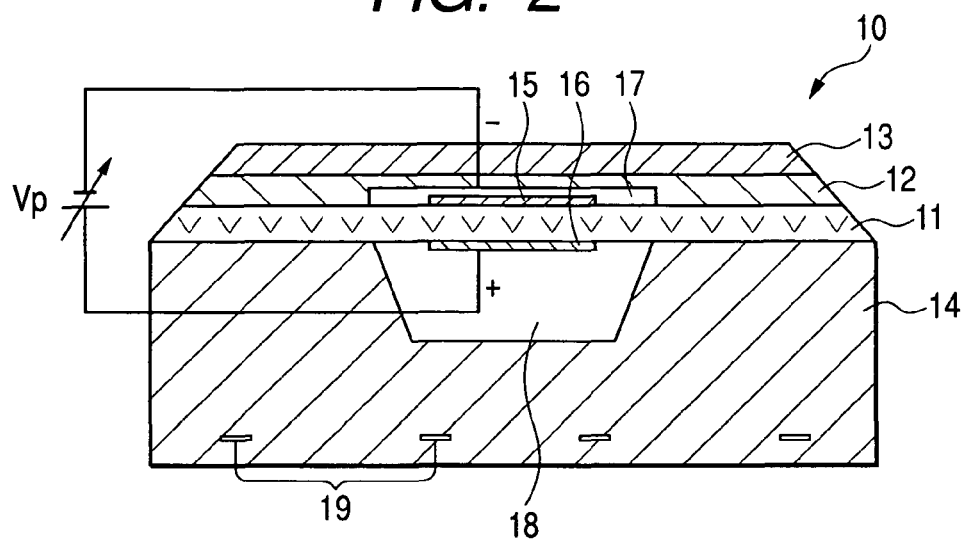
FIG. 2 is a transverse sectional view which shows a sensor device to be controlled by the gas sensor control apparatus of FIG. 1.

The sensor device 10 has a length extending perpendicular to the drawing surface of FIG. 2 and is, in practice, disposed within an assembly of a sensor housing and a protective cover. The A/F ratio sensor is installed in an exhaust pipe of the engine. For instance, EP0 987 546 A2, assigned to the same assignee as that of this application teaches a structure and control of an operation of this type of gas sensor in detail, disclosure of which is incorporated herein by reference.

The sensor device 10 is made up of a solid electrolyte layer 11, a diffusion resistance layer 12, a shielding layer 13, and an insulating layer 14 which are laminated or stacked vertically as viewed in the drawing. The sensor device 10 is surrounded by a protective layer (not shown). The solid electrolyte layer 11 is made of a rectangular partially-stabilized zirconia sheet and has upper and lower electrodes 15 and 16 affixed to opposed surfaces thereof. The diffusion resistance layer 12 is made of a porous sheet which permits the exhaust gasses to penetrate therethrough to the electrode 15. The shielding layer 13 is made of a dense sheet which inhibits the exhaust gasses from passing therethrough. The diffusion resistance layer 12 has formed therein a mixing chamber 17 to which the electrode 15 is exposed.

The diffusion resistance layer 12 and the shielding layer 13 are each formed using a sheet made of ceramic such as alumina or zirconia and have average porosities, or gas permeability different from each other.

The insulating layer 14 is made of ceramic such as alumina or zirconia and has formed therein an air duct 18 to which the electrode 16 is exposed. The insulating layer 14 has a heater 19 embedded therein. The heater 19 is made of heating wire which is supplied with power from a storage battery installed in the vehicle to heat the whole of the sensor device 10 up to a desired activation temperature.

The exhaust gasses flowing within an exhaust pipe of the engine to which the sensor device 10 is exposed enter and pass through the side of the diffusion resistance layer 12 and reach the electrode 15 within the mixing chamber 17. When the exhaust gasses are in a fuel lean state (more oxygen), oxygen molecules contained in the exhaust gasses are decomposed or ionized by application of voltage between the electrodes 15 and 16, so that they are discharged to the air duct 18 through the solid electrolyte layer 11 and the electrode 16. This will cause a positive current to flow from the electrode 16 to the electrode 15. Alternatively, when the exhaust gasses are in a fuel rich state (less oxygen), oxygen molecules contained in air within the air duct 18 are ionized by the electrode 16 so that they are discharged into the exhaust pipe through the solid electrolyte layer 11 and the electrode 15. The operation of the A/F ratio sensor is well known in the art, and explanation thereof in detail will be omitted here.

Figure 3:
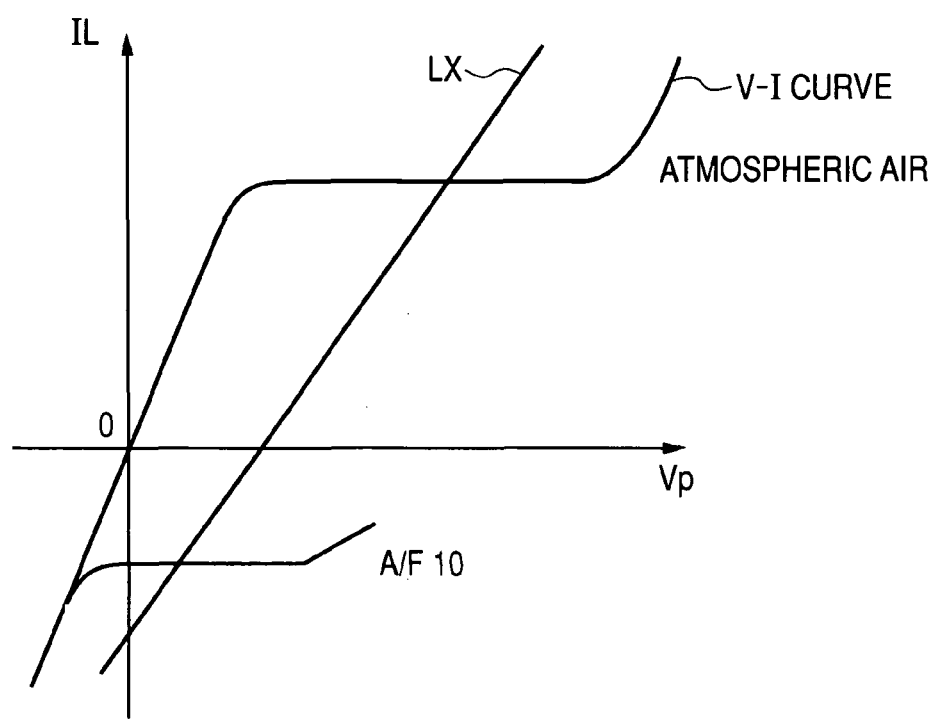
FIG. 3 is a view which shows an example of an applied voltage-to-output current map for use in determining a target voltage to be applied to the sensor device as illustrated in FIG. 2.

FIG. 3 shows a typical voltage-to-current relation (i.e., V-I characteristic) of the A/F ratio sensor. Each straight segment (i.e., a flat range) of a V-I curve extending parallel to the abscissa axis (i.e., Vp-axis) indicates a limiting current range within which the sensor device 10 produces an electric current $I_L$ (i.e., a limiting current which will also be referred to as a sensor current below) as a function of an air-fuel ratio (i.e., richness or leanness). Specifically, as the air-fuel ratio changes to the lean side, the current $I_L$ produced by the sensor device 10 increases, while as the air-fuel ratio changes to the rich side, the current $I_L$ decreases. A line LX is an applying voltage characteristic line (i.e., an applying voltage map, as represented in the form of a first-order segment) indicating a target voltage Vp to be applied to the sensor device 10 (i.e., the electrodes 15 and 16). An inclination of the line LX is almost identical with that of a portion of the V-I curve lower in voltage than the limiting current range representing a resistance-dependent range depending upon the resistance of the sensor device 10.

Referring back to FIG. 1, the air-fuel ratio measuring apparatus includes a sensor control circuit 20 in the engine ECU 1. The sensor control circuit 20 has a portion working as an ASIC (Application Specific Integrated Circuit) 2.

The sensor control circuit 20 includes a voltage application control circuit 21 connected to a positive terminal (S+ terminal) of the sensor device 10 leading to the electrode 16. The voltage application control circuit 21 is equipped with a reference voltage circuit 22, a noninverting amplifier 23, and an oscillation control capacitor 24. The reference voltage circuit 22 is connected to the noninverting amplifier 23. The noninverting amplifier 23 includes an operational amplifier 23a. The capacitor 24 is disposed between an inverting input (-input terminal) and an output of the operational amplifier 24. The noninverting amplifier 23 is equipped with an oscillation control LPF (Low Pass Filter). The reference voltage circuit 22 is equipped with a voltage divider made up of resistors $R_4$ and $R_5$ and a resistor $R_3$ connected to a junction of the resistors $R_4$ and $R_5$. Vcc denotes a constant power supply whose output is for example, 5V. The reference voltage circuit 22 may be expressed in an equivalent circuit, as illustrated at the right side of FIG. 1, which has a power supply producing a reference voltage Vref2 and a resistor $R_{345}$ which are connected in series. The reference voltage circuit 22 and the capacitor 24 are provided outside the ASIC 2.

The ASIC 2 also includes an ac voltage supply circuit 26 and a buffer 27 which are connected in series to a negative terminal (i.e., the electrode 15) of the sensor device 10 through a current-sampling resistor 28. The ac voltage supply circuit 26 works to develop and output an ac voltage at a frequency of, for example, 10 kH to 20 kH and is also equipped with an LPF through which the output is applied to the sensor device 10.

Figure 4:
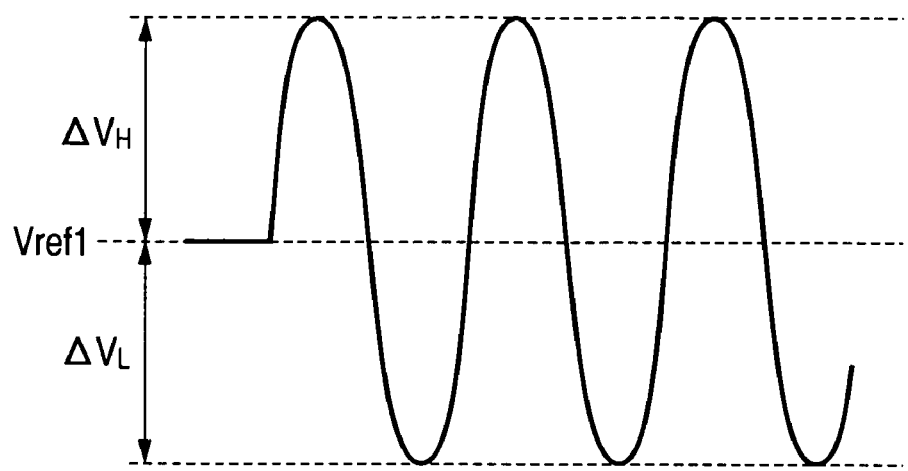
FIG. 4 is a view which shows the waveform of an voltage applied to the sensor device of FIG. 2 to measure the impedance thereof.

The ac voltage supply circuit 26 consists of an ac control circuit 26a, an ac bridge circuit 26b, and an LPF 26c. The ac voltage supply circuit 26 is designed to develop the ac voltage varying in level across the reference voltage $V_{ref1}$ in positive and negative directions alternately. The ac bridge circuit 26b is made up of resistors $R_{10}$, $R_{11}$, $R_{12}$, and $R_{13}$ and switches SW1 and SW2. The switches SW1 and SW12 are turned on alternately by the ASIC 2 to produce the ac voltage varying in level across the reference voltage $V_{ref1}$. Specifically, when the switch SW1 is turned on, and the switch SW2 is turned off, it will cause, as demonstrated in FIG. 4, the ac voltage to change or sweep to the positive side (i.e., a higher potential side) by an amplitude of $\Delta V_H$ from the reference voltage $V_{ref1}$. Conversely, when the switch SW1 is turned off, and the switch SW2 is turned on, it will cause the ac voltage to change or sweep to the negative side (i.e., a lower potential side) by an amplitude of $\Delta V_L$ from the reference voltage $V_{refl}$. The higher and lower potential amplitudes $\Delta V_H$ and $\Delta V_L$ are expressed in equations below.

$$\Delta V_H = \left(\frac{R_{11}}{R_{11} + R_{10} // R_{12}} - \frac{R_{11}}{R_{11} + R_{10}}\right) V_{CC}$$

$$\Delta V_L = \left(\frac{R_{11} // R_{13}}{R_{11} // R_{13} + R_{10}} - \frac{R_{11}}{R_{11} + R_{10}}\right) V_{CC}$$

where $R_{10}//R_{12}$ indicates a combined resistance of $R_{10}$ and $R_{12}$ (i.e., $(R_{10} \times R_{12})/(R_{10}+R_{12})$), and the same applies to $R_{11}//R_{13}$.

The current-sampling resistor 28 is disposed between the ac voltage supply circuit 26 and the sensor device 10 on a line through which the sensor current $I_L$ flows. The current-sampling resistor 28 has a resistance value $R_1$. An LPF 29 made up of a resistor and a capacitor is joined to a junction A between the current-sampling resistor 28 and the sensor device 10 (i.e., an S– terminal). The LPF 29 is also joined to a noninverting input terminal (i.e., + input terminal) of the operational amplifier 23 of the noninverting amplifier 23.

In operation, when the ac voltage supply circuit 26 applies the ac voltage to the sensor device 10 to sample the impedance of the sensor device 10, an electric current (i.e., the sensor current $I_L$) flows through the sensor device 10 which contains a component that is a function of the concentration of oxygen (i.e., an A/F ratio) of exhaust gas from the engine and a component that is a function of the impedance of the sensor device 10 (which will also be referred to as a sensor impedance below). The voltage appearing at the junction A between the current-sampling resistor 28 and the sensor device 10 changes in level in response to the cycle in which the ac voltage applied to the sensor device 10 changes in level, that is, the frequency of the ac voltage and is then inputted the noninverting amplifier 23 of the voltage application control circuit 21 through the LPF 29. Specifically, a sensor current signal (i.e., the voltage developed at the junction A) is fed to the voltage application control circuit 21 through a feedback path FB1. The voltage application control circuit 21 works to amplify the sensor current signal to control the voltage to be outputted thereby to the sensor device 10.

The sensor control circuit 20 also includes signal output circuits 31 and 32 to which the voltage is inputted which is developed at the junction A between the current-sampling resistor 28 and the sensor device 10 (i.e., the S– terminal), that is, a fraction of voltage applied across the current-sampling resistor 28 and the sensor device 10. The signal output circuit 31 is designed as an A/F signal output circuit to output an A/F ratio signal as representing an air-fuel ratio of mixture charged into the engine. The signal output circuit 32 is designed as an impedance signal output circuit to output a ZAC signal as representing the impedance of the sensor device 10. The A/F signal output circuit 31 includes a noninverting amplifier to which the voltage at the junction A is inputted through the LPF 29. Specifically, the LPF 29 works to remove an ac component of the voltage at the junction A that is a function of the impedance of the sensor device 10 from the input thereto. The LPF 29 is installed on the feedback path FB1 in order to decrease the number of terminals (i.e., pins) of the ASIC 2).

The A/F ratio signal and the ZAC signal, as outputted from the signal output circuits 31 and 32, are inputted to a microcomputer 33 of the engine ECU 1. The microcomputer 33 is of a typical structure and consists of a CPU, memories, and AD converters. The microcomputer 33 samples the A/F ratio signal and the ZAC signal through the AD converters and determines the concentration of oxygen in the exhaust gas as representing an air-fuel ratio of the mixture charged into the engine and the impedance of the sensor device 10 (will also be referred to as a sensor impedance ZAC below). The sensor impedance ZAC is used for, for example, controlling activation of the sensor device 10 through the heater 19.

The A/F signal output circuit 31 is implemented by an amplifier consisting of an LPF and an operational amplifier and works to extract from the voltage appearing at the junction A between the current-sampling resistor 28 and the sensor device 10 a dc component of the sensor current which is a function of an instant value of the air-fuel ratio of the mixture charged into the engine. The A/F signal output circuit 31 amplifies the dc component at a given amplification factor and outputs it to the microcomputer 33. The impedance signal output circuit 32 is made up of an HPF and a peak-and-hold circuit with an amplifier and works to extract from the voltage appearing at the junction A an ac component of the sensor current which is a function of an instant value of the impedance of the sensor device 10 The impedance signal output circuit 32 samples the peak of the ac component and outputs it in the form of the ZAC signal to the microcomputer 33. The amplification factors of the A/F signal output circuit 31 and the impedance signal output circuit 32 are selected independently of each other.

Usually, the output characteristics of the sensor device 10 such as the V-I characteristic, as illustrated in FIG. 3, depend upon performances of the A/F ratio sensor such as the rate at which the sensor device 10 is brought from a cold condition to a warm-up or activated condition and an output response of the sensor device 10. This may result in a difference in flat range of the output characteristic of the sensor device 10 (i.e., the V-I characteristic of the map in FIG. 3) between A/F ratio sensors, which requires the need for regulating the applying voltage characteristic of the map of FIG. 3.

Figure 5:
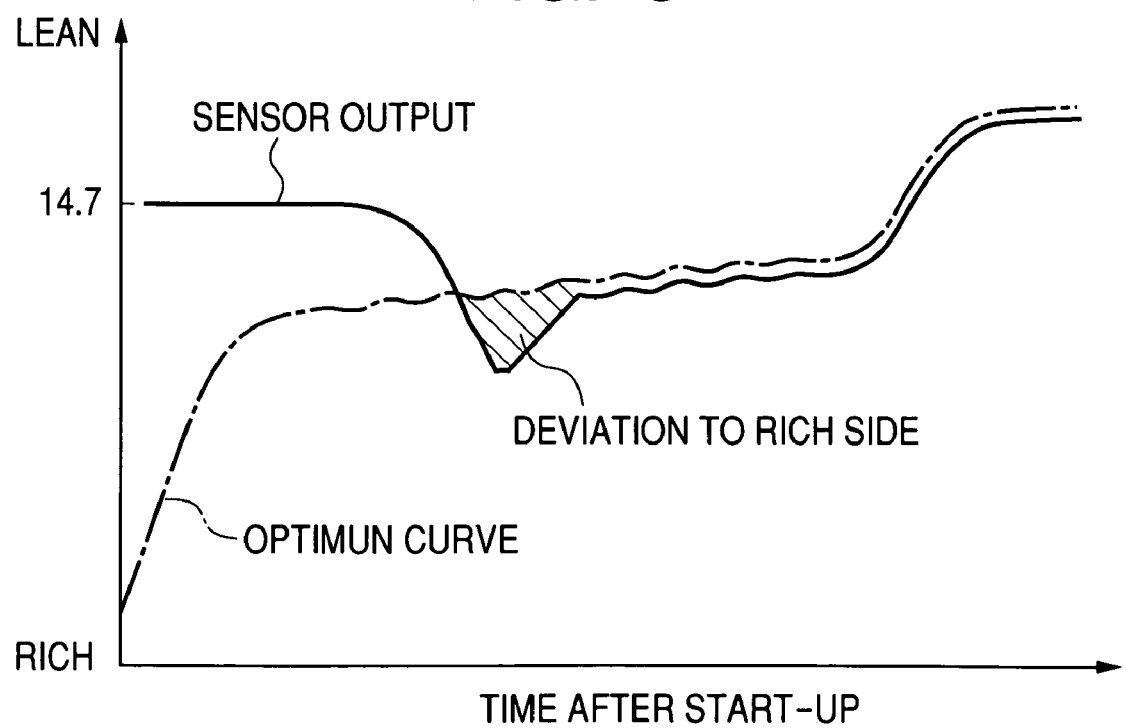
FIG. 5 is a view which demonstrates a time-sequential change in output of the sensor device of FIG. 2 immediately after start-up of an engine.

When the sensor device 10 is brought from the cold condition to the warm-up condition upon start-up of the engine, the output of the sensor device 10 will be, as illustrated in FIG. 5, normalized gradually to show a given value (the fuel rich state of the exhaust gas in the illustrated example). During such warming up of the sensor device 10, the output thereof may be deviated toward the fuel rich side. This is due to removal of organic substances such as HC from surfaces of particles of the diffusion resistance layer 12 and/or the inner wall of the mixing chamber 17 of the sensor device 10 which arises from a rise in temperature of the sensor device 10 after the start-up of the engine. Such a deviation of the output of the sensor device 10 to the fuel rich side is apt to occur, especially when the sensor device 10 is activated quickly for the purpose of reducing exhaust emissions immediately after start-up of the engine. The deviation of the output from the sensor device 10 may be avoided by increasing the size of particles of the diffusion resistance layer 12 or eliminating the mixing chamber 17. This, however, encounters the drawback in that the flat range of the output characteristic of the sensor device 10 (i.e., the V-I characteristic in FIG. 3) is narrowed.

Figure 6A:
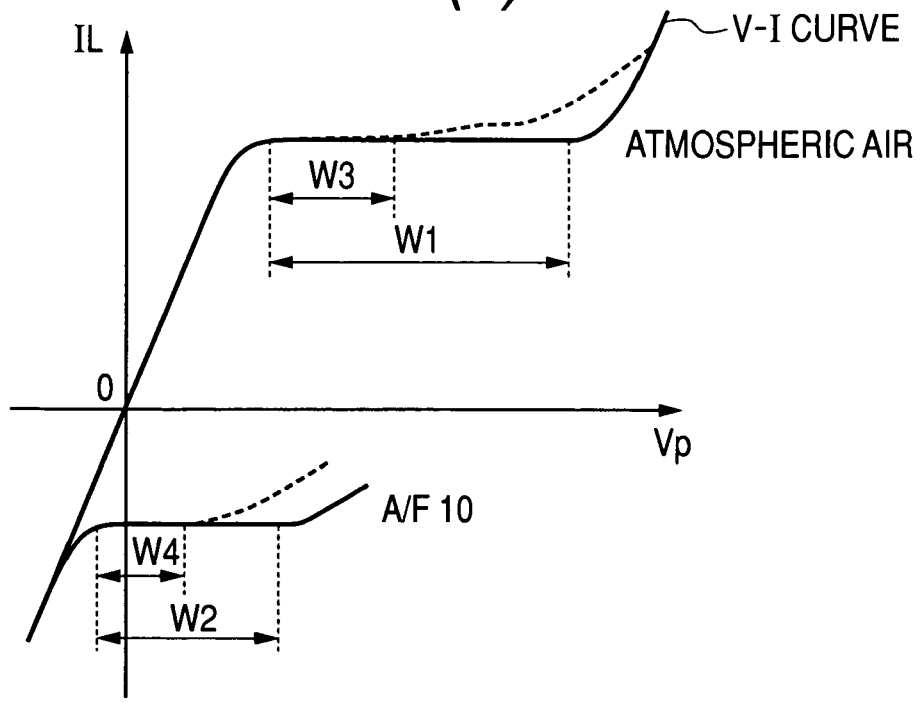
FIG. 6(a) is a view which demonstrates an output characteristic of the sensor device in FIG. 2 upon application of voltage to the sensor device.

FIG. 6(a) demonstrates the output characteristic of the sensor device 10 (i.e., the V-I curve). An upper one of straight segments of the V-I curve represents the limiting current range (i.e., the flat range) where the concentration of oxygen in the exhaust gas shows a value equivalent to that in the atmospheric air, that is, where the air-fuel ratio of the exhaust gas has a value identical with that when the engine is undergoing a fuel cut, so that only the air is being charged into the engine. The flat range has a width W1 and will also be referred to as a free-air ratio range below. A lower one of the straight segments represents a limiting current range where the air-fuel ratio of a mixture charged into the engine is 10:1. The flat range has a width W2. Broken lines represent the case where the output characteristic of the sensor device 10 is changed due to the above measures to eliminate the deviation of the output of the sensor device 10 to the fuel rich side. The upper and lower flat ranges, as indicated by the broken lines, have widths W3 and W4. Specifically, the implementation of the measures to eliminate the deviation of the output of the sensor device 10 causes the flat ranges to be narrowed from W1 to W3 and from W2 to W4.

If the applying voltage characteristic is fixed regardless of the change in output characteristic of the sensor device 10, it may cause the voltage which is out of the flat range to be applied to the sensor device 10, thus resulting in a decrease in measurement accuracy of the sensor device 10. In order to avoid this problem, the air-fuel ratio measuring apparatus of this embodiment is designed to regulate or correct the inclination and a zero-point of the applying voltage characteristic line, as discussed below, to ensure the stability of operation of the A/F ratio sensor.

Figure 6B:
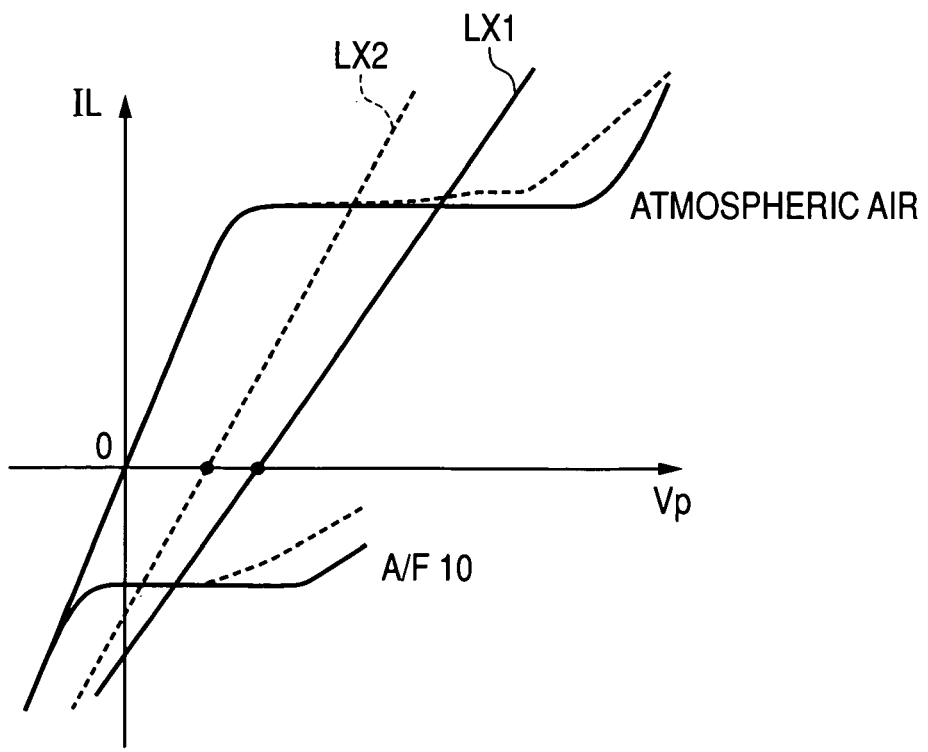
FIG. 6(b) is a view which shows how to adjust or correct an applying voltage characteristic, as expressed in the form of a first-order line, for use in determining the voltage to be applied to the sensor device of FIG. 2.

FIG. 6(b) illustrates the adjustment of the applying voltage characteristic for use in determining the voltage to be applied to the sensor device 10. In this example, the applying voltage characteristic line LX1 is changed in inclination and zero-point thereof to the applying voltage characteristic line LX2 to match the applying voltage characteristic to the A/F ratio sensor being used.

In the circuit structure of FIG. 1, the potential $V_{S+}$ appearing at the S+ terminal of the sensor device 10 and the potential $V_{S-}$ appearing at the S− terminal of the sensor device 10 are expressed by the following equations.

$$V_{S+} = \left(1 + \frac{R_2}{R_{345}}\right)(R_1 I_L + V_{ref\,1} - V_{ref\,2}) + V_{ref\,2}$$

$$V_{S-} = R_1 I_L + V_{ref\,1}$$

Assuming that $Vp=(V_{S+})-(V_{S-})$ where Vp is the voltage to be applied to the sensor device 10, the applied voltage Vp is given by $$V_P = \frac{R_2}{R_{345}} R_1 I_L + \frac{R_2}{R_{345}}(V_{ref\,1} - V_{ref\,2})$$

In the above equation, the first term "$R_2/R_{345} \cdot R_1$" on the right-hand side represents the inclination of the applying voltage characteristic line LX. The second term "$R_2/R_{345} \cdot (V_{ref1}-V_{ref2})$" on the right-hand side represents the zero-point of the applying voltage characteristic line LX (i.e., the voltage to be applied to the sensor device 10 when the sensor current $I_L=0$ mA).

The resistance value $R_{345}$ in the term "$R_2/R_{345} \cdot R_1$" representing the inclination of the applying voltage characteristic line LX is the resistance value in the reference voltage circuit 22 disposed outside the ASIC 2, so that it may be regulated easily independently of the ASIC 2.

The amplification factor of the noninverting amplifier 23 may be regulated by changing the resistance value $R_{345}$, thereby changing the inclination of the applying voltage characteristic line, in other words, the relation between the sensor current $I_L$ and the voltage to be applied to the sensor device 10. The current-sampling resistor 28 is also disposed outside the ASIC 2, so that the resistance value thereof may be regulated easily. The sensor current $I_L$ is, however, responsive to the change in resistance value $R_1$ of the current-sampling resistor 28, so that use of the current-sampling resistor 28 to change the inclination of the applying voltage characteristic line is not recommended.

As apparent from the above, the reference voltage circuit 22 (i.e., the voltage application control circuit 21) is disposed to be separate from the current-sampling resistor 28 and the ac voltage supply circuit 26, thereby permitting the amplification factor of the noninverting amplifier 23 to be altered without impinging upon operations of other parts.

The term "$R_2/R_{345} \cdot (V_{ref1}-V_{ref2})$" representing the zero-point of the applying voltage characteristic line LX may be regulated by changing the reference voltage $V_{ref2}$ which is one of the two reference voltages $V_{ref1}$ and $V_{ref2}$. The reference voltage $V_{ref2}$ is the voltage, as developed by a fraction of the output of the constant power supply Vcc created by the resistors $R_4$ and $R_5$. The reference voltage $V_{ref2}$ is expressed by $$V_{ref\,2} = \frac{R_5}{R_4 + R_5} Vcc$$

The changing of the reference voltage $V_{ref2}$ is achieved by altering the resistance values $R_4$ and $R_5$ of the voltage divider. The reference voltage circuit 22 is, as described above, disposed to be separate from the ASIC 2, thereby permitting the reference voltage $V_{ref2}$ to be altered easily.

As already described, the reference voltage circuit 22 (i.e. the voltage application control circuit 21) is separate from the current-sampling resistor 28 and the ac voltage supply circuit 26, thus permitting the reference voltage $V_{ref2}$ to be regulated to adjust the zero-point of the applying voltage characteristic line LX to a desired voltage value without impinging upon operations of other parts.

In the above described manners, the sensor control circuit 20 is permitted to regulate the inclination and/or the zero-point of the applying voltage characteristic line LX in the map of FIG. 3 used to determine the voltage to be applied to the sensor device 10 as needed to ensure the stability of operation of the A/F ratio sensor to assure the accuracy of an output to the microcomputer 33. For example, the regulation of the inclination and/or the zero-point of the applying voltage characteristic may be achieved in bench-tests before shipment of the engine ECU 1. Such regulation is made preferably by monitoring the output characteristic of the sensor device 10 to be used and correcting the applying voltage characteristic line LX of the map in FIG. 3, as stored in the sensor control circuit 20, to bring the voltage to be applied to the sensor device 10 to fall within a corresponding one of the flat ranges (i.e., the limiting current ranges) based on the monitored output characteristic of the sensor device 10.

When it is required to alter the zero-point of the applying voltage characteristic line LX, there is no need for the reference voltage $V_{ref1}$, thus ensuring the altering of the zero-point without sacrificing the accuracy of the sensor current $I_L$. Specifically, the altering of the reference voltage $V_{ref1}$ results in an offset error of the sensor current $I_L$ and requires the need for regulating the resistance values of the ac bridge circuit 26b, which consumes operator's time undesirably, and also the need for installing additional terminals to the ASIC 2 for regulating the resistance values.

Figure 7:
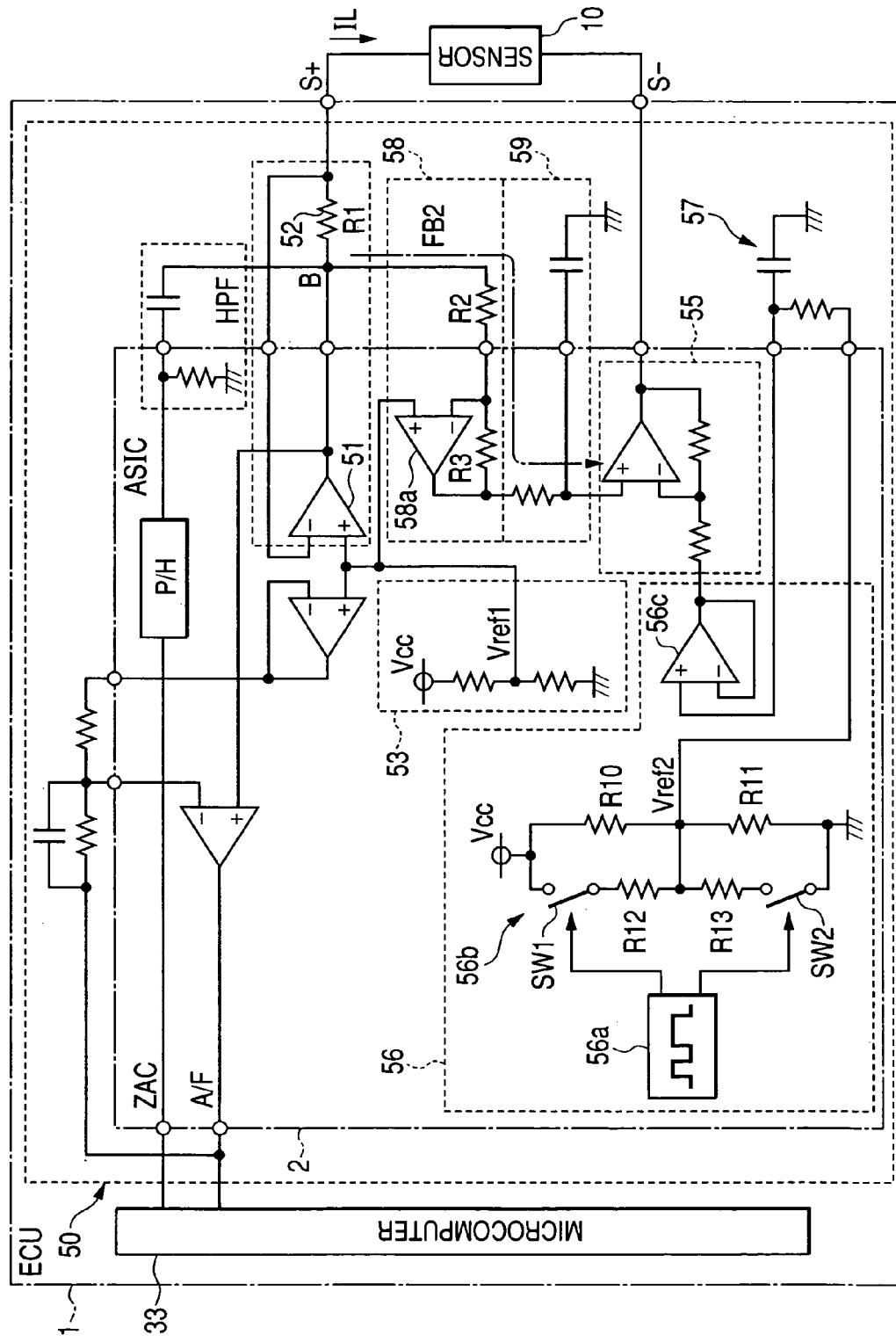
FIG. 7 is a circuit diagram which shows an electric structure of an example of one of conventional gas sensor control apparatuses.

FIG. 7 illustrates an example of one of conventional sensor control circuits for use in air-fuel ratio control systems for comparison with the sensor control circuit 20 of FIG. 1.

The sensor control circuit 50 has a reference voltage circuit 53 connected to the S+ terminal of the sensor device 10 through an operational amplifier 51 and a current-measuring resistor (i.e., a shunt resistor) 52. The reference voltage circuit 53 works to makes a fraction of an output of the constant power supply Vcc to produce the reference voltage $V_{ref1}$. The ac power supply circuit 56 is connected to the S− terminal of the sensor device 10 through the voltage application control circuit 55 made by a noninverting amplifier. A LPF 57 is installed at an output stage of the ac power supply circuit 56 outside the ASIC 2. The ac power supply circuit 56 is made up of an ac control circuit 56a, an ac bridge circuit 56b, and a buffer 56c and works to develop an ac voltage having an amplitude oscillating across the reference voltage $V_{ref2}$ to the positive and negative side cyclically. The ac bridge circuit 56b is identical in structure with the ac bridge circuit 26b in FIG. 1.

The voltage appearing at a junction B leading to one of ends of the current-measuring resistor 52 changes with a change in the sensor current $I_L$. The voltage at the junction B is inputted to the voltage application control circuit 55 through the noninverting amplifier 58 and the LPF 59. The resistor R2 and R3 are connected to the operational amplifier 58a of the noninverting amplifier 58. The voltage application control circuit 55 works to control the voltage to be applied to the sensor device 10 as a function of the voltage created at the junction B (i.e., a sensor current signal). Specifically, the sensor current signal (i.e., the voltage developed at the junction B) is fed to the voltage application control circuit 55 through a feedback path FB2.

In the circuit structure of FIG. 7, the potential $V_{S+}$ appearing at the S+ terminal of the sensor device 10 and the potential $V_{S-}$ appearing at the S− terminal of the sensor device 10 are expressed by the following equations.

$$V_{S+} = V_{ref\,1}$$

$$V_{S-} = -2\left(\frac{R_3}{R_2}\right)R_1 I_L + 2V_{ref\,1} - V_{ref\,2}$$

Assuming that $Vp=(V_{S+})-(V_{S-})$ where Vp is the voltage to be applied to the sensor device 10, the applied voltage Vp is given by $$V_P = 2\frac{R_3}{R_2}R_1 I_L - V_{ref\,2} - V_{ref\,1}$$

In the above equation, the first term "$2 \cdot R_3/R_2 \cdot R_1$" on the right-hand side represents the inclination of the applying voltage characteristic line LX. The second term "($V_{ref2}-V_{ref1}$)" on the right-hand side represents the zero-point of the applying voltage characteristic line LX (i.e., the voltage to be applied to the sensor device 10 when the sensor current IL=0 mA).

The adjustment of the inclination of the applying voltage characteristic line LX (i.e., 2·R₃/R₂·R₁) may be achieved by installing the resistor R2 that is one of the resistors R1 and R2 constituting the noninverting amplifier 58 outside the ASIC 2.

The reference voltages $V_{ref2}$ and $V_{ref1}$ used in the term "$V_{ref2}-V_{ref1}$" representing the zero-point of the applying voltage characteristic line LX are both difficult to change, thus resulting in a difficulty in adjusting the zero-point to a desired position. The changing of the reference voltage $V_{ref1}$ may result in an offset error of the sensor current $I_L$. The changing of the reference voltage $V_{ref2}$ will results in a change in amplitude of the voltage outputted from the ac power supply circuit 56. In other words, in order to alter the reference voltage $V_{ref2}$ with no effects on the amplitude of the voltage to be outputted by the ac power supply circuit 56, it is necessary to install the resistors of the bridge circuit 56b outside the ASIC 2. It is, therefore, difficult for the structure of FIG. 7, to regulate both the inclination and the zero-point of the applying voltage characteristic line LX to correct the output characteristic of the sensor device 10.

The structure of the sensor control apparatus in FIG. 1 has the following advantages.

The reference voltage circuit 22 (i.e., the voltage application control circuit 21) is disposed independently of the current-sampling resistor 28 and the ac voltage supply circuit 26, thereby permitting the reference voltage $V_{ref2}$ to correct the zero-point of the applying voltage characteristic line LX easily with no adverse effects on other operations of the sensor control apparatus. The inclination of the applying voltage characteristic line LX may also be corrected by regulating the reference voltage circuit 22. This facilitates ease of matching the control of the voltage to be applied to the sensor device 10 to the operational property (i.e., the output characteristic) thereof, thereby enabling the voltage lying within the flat range (i.e., the limiting current range) of the output characteristic of the sensor device 10 to be applied to the sensor device 10 in each of the A/F ratio measuring ranges. This ensures the accuracy in measuring the air-fuel ratio of a mixture charged into the engine over a wide range.

Particularly, in a sensor device in which the size of particles of the diffusion resistance layer 12 or the mixing chamber 17 is omitted in order to accelerate the activation of the sensor device or assure the stability of output from the sensor device (i.e., eliminate the deviation of the output of the sensor device 10 to the rich side) during warm-up of the sensor device, the flat ranges may be, as described above, narrowed undesirably. The structure of the sensor control apparatus of this embodiment is very useful for such a type of sensor device.

The ASIC 2 is designed to include the ac voltage supply circuit 26. The reference voltage circuit 22 of the voltage application control circuit 21 is installed outside the ASIC 2. The reference voltage circuit 22 is also designed to create a fraction of the output of the constant power supply Vcc to produce the reference voltage $V_{ref2}$, thereby facilitating the ease of adjustment of the reference voltage $V_{ref2}$. This achieves the correction of the inclination and the zero-point of the applying voltage characteristic line LX of the output characteristic of the sensor device 10 with ease.

The reference voltage $V_{ref1}$ needs not to be corrected, thus resulting in no need for installing additional terminals to the ASIC 2, which permits the ASIC 2 to be reduced in size and results in a decrease in cost of the ASIC 2 as compared with the conventional structure of FIG. 7.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modifications to the shown embodiment witch can be embodied without departing from the principle of the invention as set forth in the appended claims.

For instance, the sensor control circuit 20 may alternatively be designed to correct only the zero-point of the applying voltage characteristic line LX.

The voltage application control circuit 21 has only the reference voltage circuit 22 installed outside the ASIC 2, but may alternatively be designed to have all the component parts thereof installed outside the ASIC 2. In terms of production costs of the sensor control circuit 20, it is, however, advisable that as many as possible of the component parts of the voltage application control circuit 21 be fabricated on an IC.

The ac voltage supply circuit 26 outputs the ac voltage at all times, but may alternatively be designed to output it as required. For example, the ac voltage supply circuit 26 may work to output the ac voltage at a time interval preselected to sample the impedance ZAC of the sensor device 10.

The sensor device 10 has a single cell type, but may alternatively be designed to have two cells: a pump cell and an electromotive force cell. In other words, the sensor device 10 may have two layers or three layers of solid electrolyte. The sensor device 10 may also be designed to be of a cup-shape as is well known in the art.

The sensor control circuit 20 may be used with a gas sensor designed to measure the concentration of gas other than oxygen instead of the A/F ratio sensor. For example, a composite sensor may be used which includes first cell (i.e., a pump cell) and a second cell (i.e., a sensor cell) which are made of a solid electrolyte body. The first cell works as the pump cell to pump oxygen molecules out of or into a first gas chamber formed in a sensor body and output a signal indicative of the concentration of the pumped oxygen molecules. The second cell works as the sensor cell to produce a signal indicative of the concentration of a preselected component of gasses flowing into a second gas chamber from the first gas chamber. For example, the composite gas sensor may be used to measure the concentration NOx contained in exhaust gasses of the automotive engine. Further, the composite gas sensor may be designed to have a third cell serving as a monitor cell or a second pump cell to produce an electric signal as a function of concentration of oxygen molecules remaining in the second gas chamber.

The sensor control apparatus may alternatively be used with a gas sensor working to measure the concentration of HC or CO contained in the exhaust gasses of the automotive engine. The measurement of concentration of HC or CO is achieved by pumping excessive oxygen ($O_2$) out of the first gas chamber using the pump cell and decomposing HC or CO contained in the gasses entering the second gas chamber using the sensor cell to produce an electric signal indicative of the concentration of HC or CO.

The sensor control apparatus may be used with gas sensors for diesel engines as well as gasoline engines. The sensor control apparatus may also be used to measure the concentration of gas other than exhaust gas from automotive engines.

What is claimed is:

1. A gas sensor control apparatus designed to control an operation of a gas sensor device equipped with a solid electrolyte body and a first and a second electrode affixed to opposed surfaces of the solid electrolyte body, comprising:

a sensor current sampling resistor connected in series to a first terminal that is one of a positive and a negative terminals which leads to the first electrode of the gas sensor device;

a first voltage supply circuit configured to develop a first voltage based on a first reference voltage at the first terminal leading to the gas sensor device through said sensor current sampling resistor;

a second voltage supply circuit configured to develop a second voltage based on a second reference voltage at a second terminal that is other of the positive and negative terminals which leads to the second electrode of the gas sensor device; and a controller configured to sample through said sensor current sampling resistor a sensor current that is an electric current flowing through the gas sensor device upon application of voltage across the gas sensor device through the first and second terminals resulting from development of the first and second voltage at the first and second terminals and to produce a signal based on the sensor current which is a function of concentration of a given gas, when it is required to measure an impedance of the gas sensor device, said controller alternating the first voltage across the first reference voltage and sampling and outputting a resulting change in the sensor current as representing the impedance of the gas sensor device;

wherein said second voltage supply circuit is configured to amplify the sensor current, as sampled through said sensor current sampling resistor, to control the second voltage, as developed at the second terminal.

2. A gas sensor control apparatus as set forth in claim 1, further comprising an integrated circuit (IC) on which said first voltage supply circuit is fabricated, and wherein said second voltage supply circuit has a reference voltage circuit which is configured to create the second reference voltage and is located outside the integrated circuit (IC).

3. A gas sensor control apparatus as set forth in claim 1, wherein said second voltage supply circuit includes a voltage divider which has a resistor to produce a fraction of an output of a constant voltage source to create the second reference voltage.

4. A gas sensor control apparatus as set forth in claim 1, wherein said first voltage supply circuit includes a bridge circuit made up of four resistors and a first and a second switches disposed at a high potential side and a low potential side of the bridge circuit, respectively, and wherein said controller turns on and off the first and second switches alternatively to alternate the first voltage across the first reference voltage.

5. A method of controlling a voltage to be applied to a gas sensor device equipped with a solid electrolyte body and a first and a second electrode affixed to opposed surfaces of the solid electrolyte body through a gas sensor control apparatus which includes (a) a sensor current sampling resistor connected in series to a first terminal that is one of a positive and a negative terminals which leads to the first electrode of the gas sensor device, (b) a first voltage supply circuit configured to develop a first voltage based on a first reference voltage at the first terminal leading to the gas sensor device through said sensor current sampling resistor, (c) a second voltage supply circuit configured to develop a second voltage based on a second reference voltage at a second terminal that is other of the positive and negative terminals which leads to the second electrode of the gas sensor device, and (d) a controller configured to control the second voltage to determine and apply a voltage across the gas sensor device through the first and second terminals based on a given applying voltage characteristic and to sample through said sensor current sampling resistor a sensor current that is an electric current flowing through the gas sensor device resulting from application of the voltage across the gas sensor device to produce a signal based on the sensor current which is a function of concentration of a given gas, when it is required to measure an impedance of the gas sensor device, said controller alternating the first voltage across the first reference voltage and sampling and outputting a resulting change in the sensor current as representing the impedance of the gas sensor device, said method comprising:

sampling an output characteristic of the gas sensor device; and correcting the applying voltage characteristic based on the sampled output characteristic so as to bring the voltage applied to the gas sensor device into agreement with a desired one;

amplifying, using the second voltage supply circuit, the sensor current, as sampled through said sensor current sampling resistor, to control the second voltage, as developed at the second terminal.

* * * * *